Figure 1:
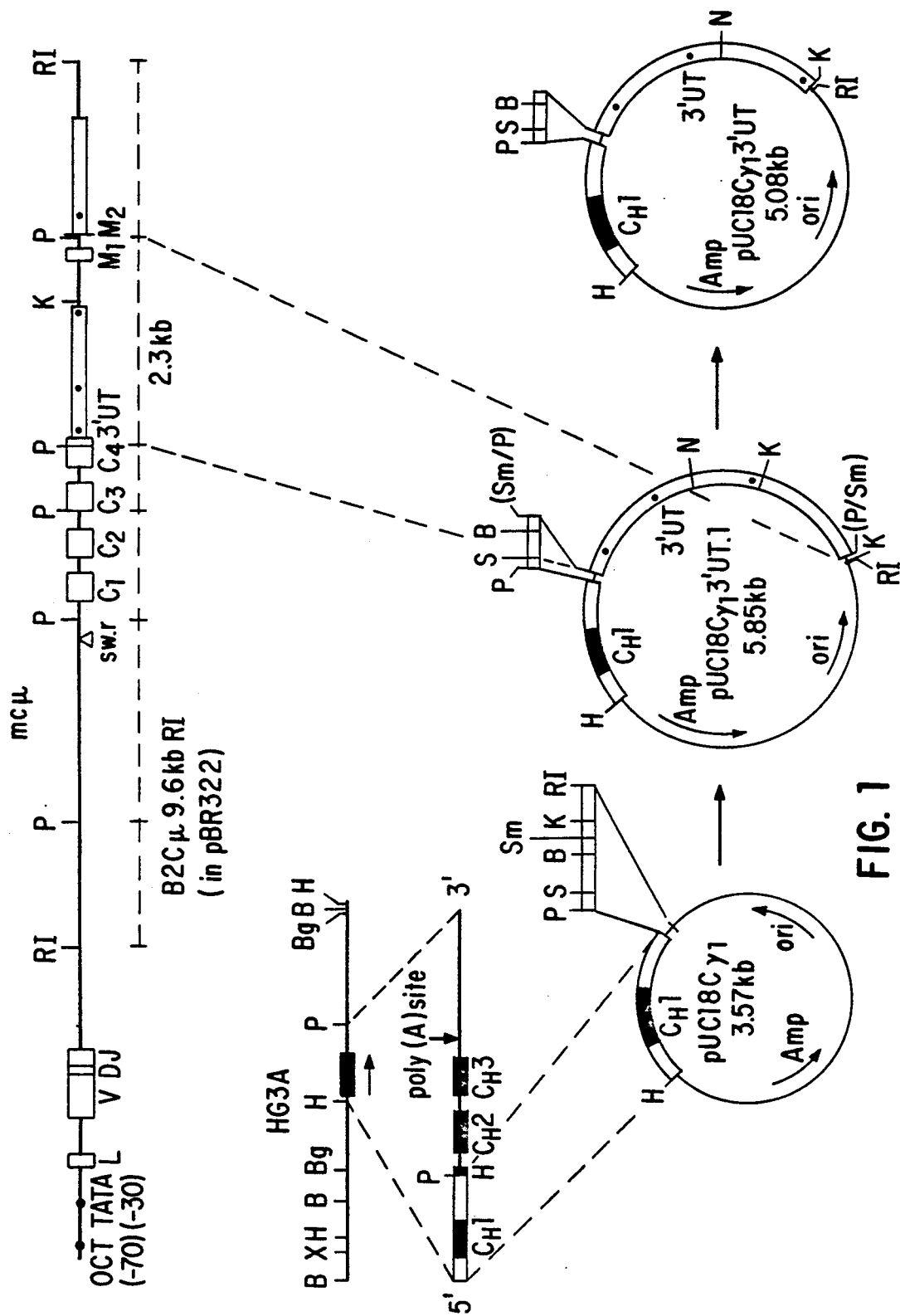

United States Patent [19]
Fell, Jr. et al.

[11] Patent Number: 5,314,995
[45] Date of Patent: May 24, 1994

[54] THERAPEUTIC INTERLEUKIN-2-ANTIBODY BASED FUSION PROTEINS

[75] Inventors: Henry P. Fell, Jr., Redmond; Margit A. Gayle, Woodinville, both of Wash.

[73] Assignee: Oncogen, Seattle, Wash.

[21] Appl. No.: 468,390

[22] Filed: Jan. 22, 1990

[51] Int. Cl.⁵ ............................................. C07K 13/00
[52] U.S. Cl. ................... 530/351; 530/387.1; 530/387.3; 530/387.7; 530/388.3; 530/388.4; 530/388.5; 530/388.6; 530/388.8; 530/388.85; 530/391.7; 530/391.9; 435/69.5; 435/69.52; 435/69.7; 435/70.2; 435/70.21; 424/85.8; 424/85.1; 424/85.2; 424/85.91; 935/47

[58] Field of Search ............... 530/387, 389–391, 530/808, 810, 351, 387.1, 387.3, 387.7, 388.3–388.6, 388.8, 388.85, 391.7, 391.9, 866, 867; 435/69.5, 69.52, 69.7, 70.2, 70.21; 935/47; 424/85.8, 85.1, 85.2, 85.91

[56] References Cited

U.S. PATENT DOCUMENTS
4,935,352  6/1990  Koichi et al. .................... 435/69.52
5,095,096  3/1992  Miki et al. ........................... 530/351

FOREIGN PATENT DOCUMENTS
305967   3/1989  European Pat. Off.
332174   9/1989  European Pat. Off. ...... C07K 13/00
367166   5/1990  European Pat. Off.
0396387 11/1990  European Pat. Off.
WO86/01533 3/1986  PCT Int'l Appl. ......... C12N 15/00
9101004  1/1991  PCT Int'l Appl.

OTHER PUBLICATIONS

Ikeyama, Mol. Immunol., vol 24(10), 1987, pp. 1039–1046.
Chaudhary et al., 1989, Nature, 339:394–397.
Hellstrom et al., 1984, in Monoclonal Antibodies and Cancer, Wright et al. (eds.), Marcel Dekker, Inc., N.Y., pp. 31–47 ("Hellstrom I").
Hellstrom et al., 1985, in Monoclonal Antibodies for Cancer Detection and Therapy, Baldwin et al. (eds.), Academic Press, N.Y., pp. 17–51 ("Hellstrom II").
Kelley et al., 1988, Proc. Natl. Acad. Sci. USA, 85:3980–3984.
Kirkman et al., 1989, Transplantation, 47, (No. 2):327–330.
Kiyokawa et al., 1989, Cancer Res., 49:4042–4046.
Morrison et al., 1984, Proc. Natl. Acad. Sci. USA, 81:6851–6855 ("Morrison I").
Morrison, 1985, Science, 229:1202–1207 ("Morrison II").
Murphy, 1988, in Immunotoxins, Frankel (ed.), Kluwer Academic Publishers, pp. 123–140.
Neuberger et al., 1984, Nature, 312:604–608.
Roberge et al., 1989, J. Immunol., 143, (No. 11): 3498–3502.
Sahagan et al., J. Immunol., 137, (No. 3): 1066–1074.
Sun et al., 1987, Proc. Natl. Acad. Sci. USA, 84:214–218.
Walz et al., Jan. 1990, Transplantation, 49, (No. 1): 198–201.
Williams et al., 1986, Gene, 43:319–324.
Sasada et al., Cell Structure and Function, 13, 1988, pp. 129–141.
Senoo et al., CA, vol. 104, 1986, #220129c.
Gross et al., PNAS 86, 1989, pp. 10024–10028.
Ashenozi et al., CA, vol. 116(3), 1991, #19532h.
Morrison et al., CA, 116(3), 1991, #19660a.
Schnee et al., PNAS, vol. 84, No. 1987, pp. 6904–6908.
Traunecker et al., Nature, 339, 1989, pp. 68–70.

Primary Examiner—Garnette D. Draper
Attorney, Agent, or Firm—Pennie & Edmonds

[57] ABSTRACT

The present invention relates to antibody-based fusion proteins wherein a portion of an immunoglobulin molecule is linked to a biologically active ligand. In particular embodiments of the invention, the fusion protein comprises a portion of an antibody which recognizes a cell surface antigen linked to a ligand which is a lymphokine or a cellular factor. A preferred embodiment of the fusion protein comprises the variable region of the anti-tumor monoclonal antibody L6 and an active lymphokine molecule such as IL-2. In another preferred embodiment of the present invention, the fusion protein comprises the variable region of the L6 monoclonal antibody and active platelet factor 4. The antibody-based fusion proteins of the invention may be used therapeutically to deliver biologically active ligands to a specific target cell or tissue.

3 Claims, 10 Drawing Sheets

Exact Hinge Sequences

HINGE

```
  E   P   K   S   C   D   K   T   H   T   P   P   S   P   G   R   V   V   G   G   R   A
  GAG CCC AAA TCC TGT GAC AAA ACT CAC ACA CCG CCA TCC CCA GGA AGA GTG GTG GGC GGG CG
  ACGT CTC GGG TTT AGG ACA CTG TTT TGA GTG TGT GGC GGT GGC AGG GGT CCT TCT CAC CAC CCG CCC GC TC GG
```

IL2:
```
    T
    ACG
    TGC
```

Onco M:

Onco P:
```
        Q           R
        CAG         CGA
        GTC         GCT
```

F(ab')₂:
```
        C           C       Stop
        TGC         TGC     TGA
        ACG         ACG     ACT
```

Exact Hinge - Gene Linker Sequences

IL2
```
  A   V   L   R   A   M
  A GCC GTA CTG CGC GC
    CAT GAC GCC CGG TAC
```

FIG.7

Preparation of total cellular RNA from 5x10[7] CD3/CD28 stimulated PBLs (6 hr stimulation).

Single strand cDNA by reverse transcriptase using IL2-3' primer

Polymerase chain reaction using ILS2-5' and IL2-3' primers

IL2-5'          Nco I
   G TCA ACC ATG GCA CCT ACT TCA AGT TCT ACA AAG
...GTC ACA AAC AGT GCA CCT ACT TCA AGT TCT ACA AAG AAA ACA CAG....342 nucl........

Stop
IL2 mRNA         ...CAAAGCATCATCTCAACACTAACTTGATAATTAAGTGC...
                    GTTTCGTAGTAGAGTTGTGATTGAACTCCTAGGAAGTC Blunt end ligation into pUC19 (SmaI site) confirmation of sequence Digestion with NcoI + BamHI for placement of pUCCγ1 3'UT vector with hinge and polylinker oligos.

FIG.8

Human mRNA encoding interleukin-2 (IL-2)

```
                                                   M   Y   R   M
ATCACTCTCT TTAATCACTA CTCACAGTAA CCTCAACTCC TGCCACAATG TACAGGATGC   60

Q  L  L   S  C  I  A   L  S  L   A  L  V  T   N  S  A   P  T  S
AACTCCTGTC TTGCATTGCA CTAAGTCTTG CACTTGTCAC AAACAGTGCA CCTACTTCAA  120

S  S  T   K  K  T  Q   L  Q  L  E   H  L   L  L  D  L   Q  M  I
GTTCTACAAA GAAAACACAG CTACAACTGG AGCATTTACT GCTGGATTTA CAGATGATTT  180

L  N  G   I  N  N  Y   K  N  P   K  L  T   R  M  L  T   F  K  F
TGAATGGAAT TAATAATTAC AAGAATCCCA AACTCACCAG GATGCTCACA TTTAAGTTTT  240

Y  M  P   K  K  A  T   E  L  K  H   L  Q   C  L  E  E   E  L  K
ACATGCCCAA GAAGGCCACA GAACTGAAAC ATCTTCAGTG TCTAGAAGAA GAACTCAAAC  300

P  L  E   E  V  L  N   L  A  Q  S   K  N   F  H  L  R   P  R  D
CTCTGGAGGA AGTGCTAAAT TTAGCTCAAA GCAAAAACTT TCACTTAAGA CCCAGGGACT  360

L  I  S   N  I  N  V   I  V  L   E  L  K   G  S  E  T   T  F  M
TAATCAGCAA TATCAACGTA ATAGTTCTGG AACTAAAGGG ATCTGAAACA ACATTCATGT  420

C  E  Y   A  D  E  T   A  T  I  V   E  F   L  N  R  W   I  T  F
GTGAATATGC TGATGAGACA GCAACCATTG TAGAATTTCT GAACAGATGG ATTACCTTTT  480

C  Q  S   I  I  S  T   L  T
GTCAAAGCAT CATCTCAACA CTAACTTGAT AATTAAGTGC TTCCCACTTA AAACATATCA  540

GGCCTTCTAT TTATTTAAAT ATTTAAATTT TATATTTATT GTTGAATGTA TGGTTTGCTA  600

CCTATTGTAA CTATTATTCT TAATCTTAAA ACTATAAATA TGGATCTTTT ATGATTCTTT  660

TTGTAAGCCC TAGGGGCTCT AAAATGGTTT CACTTATTTA TCCCAAAATA TTTATTATTA  720

TGTTGAATGT TAAATATAGT ATCTATGTAG ATTGGTTAGT AAAACTATTT AATAAATTTG  780

ATAAATATAA AAAAAAAAA C                                             801
```

FIG.9

5,314,995

THERAPEUTIC INTERLEUKIN-2-ANTIBODY BASED FUSION PROTEINS

1. INTRODUCTION

The present invention relates to antibody based proteins in which a portion of an antibody is fused to a biologically active ligand. The resulting fusion protein may be used to deliver the active molecule to a specific target cell or tissue. In particular embodiments of the present invention, a portion of an antibody which recognizes a tumor cell is linked to a ligand which is an anti-tumor agent. In a preferred embodiment of the present invention, a portion of an antibody which recognizes a tumor cell is linked to a lymphokine such as IL-2, thereby providing a method for producing a targeted, amplified anti-tumor immune response.

2. BACKGROUND OF THE INVENTION

2.1. MONOCLONAL ANTIBODIES AS DIAGNOSTIC AND THERAPEUTIC REAGENTS

Since the development of the cell fusion technique for the production of monoclonal antibodies (Kohler and Milstein, 1975, Nature 256:495), a vast number of monoclonal antibodies, many of which define heretofore unknown antigens, have been produced by a number of researchers. Concurrently, a number of techniques have been developed for the generation of monoclonal antibodies, including the B cell hybridoma technique (Kozbor et al, 1983, Immunology Today 4:72) and the EBV hybridoma technique to produce human monoclonal antibodies (Cole et al., 1985, in "Monoclonal Antibodies and Cancer Therapy," Alan R. Liss, Inc. pp. 77-96).

Through hybridoma technology, monoclonal antibodies (Mab) can be developed that are capable of recognizing almost any determinant or epitope. The property of specific recognition and binding to particular cells has encouraged the development of Mabs as diagnostic and therapeutic reagents for a variety of disease states. Mabs have been obtained that recognize determinants preferentially expressed on tumor cells (Hellstrom et al., 1984 in "Monoclonal Antibodies and Cancer", Wright et. al. Marcel Dekker, Inc., N.Y., pp. 31-47) and are currently being evaluated in the clinic for their effectiveness as therapeutic agents.

2.2. USE OF MONOCLONAL ANTIBODIES AS TARGETING AGENTS

The ability of monoclonal antibodies (Mabs) to localize to tumor tissue has also led to the development of Mabs conjugated to various substances in an effort to target specific molecules to tumor sites (Hellstrom and Hellstrom, 1985, in "Monoclonal Antibodies for Tumor Detection and Drug Targeting," Baldwin et al. eds, Academic Press, N.Y. pp. 17-51). Linkages have been performed using toxins, drugs, radionuclides, and enzymes for the activation of prodrug compounds. Many of these linkages involve the chemical conjugation of the reactive moiety with a given preparation of antibody, a process which can be cumbersome and subject to variation. (U.S. Pat. No. 4,671,958 by Rodwell et al., filed Mar. 9, 1982, issued Jun. 9, 1987).

Recently, recombinant DNA techniques have been used to produce genetically altered immunoglobulin molecules. For example, techniques have been developed to produce chimeric antibodies, which combine regions of immunoglobulin molecules from different sources (Morrison et al., 1984, Proc. Natl. Acad. Sci. U.S.A. 81:6581; Sahagan et al., 1986, J. Immunol. 137:1066; Sun et al., 1987, Proc. Natl. Acad. Sci. U.S.A. 84:214). Usually, chimeric antibodies combine an antigen-combining region (or variable region) from a non-human source and a constant region from a human source.

Chimeric antibody technology has been extended to produce chimeric molecules comprising immunoglobulin and non-immunoglobulin portions. For example, International Patent Application No. PCT/GB85/00392 by Neuberger et al., filed Sep. 3, 1985, and published Mar. 13, 1986, describes the production of Fab-*Staphylococcus aureus* nuclease, Fab-myc, and Fab-Klenow fragment of DNA polymerase I chimeric antibodies (see also Neuberger et al., 1984, Nature 312:604-608 and Williams and Neuberger, 1986, Gene 43:319-324). Schnee et al. (1987, Proc. Natl. Acad. Sci. U.S.A. 84:6904-6908) describe the construction of a hybrid molecule comprising the variable region of an anti-fibrin antibody and the catalytic β-chain of tissue plasminogen activator.

3. SUMMARY OF THE INVENTION

The present invention relates to a system for the generation of antibody fusion proteins which has utility in the production of recombinant molecules that possess novel, clinically relevant biological activity. The antibody fusion proteins of the invention may be used therapeutically to deliver biologically active ligands to a desired tissue.

In particular embodiments of the invention, the antibody fusion protein comprises a biologically active ligand which is a lymphokine, including, in a specific embodiment, interleukin-2. Because interleukin-2 induces lymphocyte proliferation, fused antibody that targets interleukin-2 (IL-2) to a malignant or infected tissue can produce localized amplification of the immune response toward the diseased tissue, and thereby facilitate the destruction of the infected or malignant tissue. In a specific embodiment of the invention, a fused antibody is produced which comprises a variable region of the anti-tumor antigen monoclonal antibody L6 and active IL-2.

Additional embodiments of the invention relate to fused antibodies which comprise an immunoglobulin variable region and a biologically active ligand which is a non-lymphokine cellular factor. In a specific embodiment of the invention, a fused antibody is produced which comprises a variable region of the anti-tumor antigen monoclonal antibody L6 and active platelet factor 4, a molecule associated with antagonism of angiogenesis, inhibition of suppressor T lymphocyte development, chemotaxis and heparin binding.

4. DESCRIPTION OF THE FIGURES

FIG. 1. Diagram of insertion of $CH_1$ into pUC18 vector.

Figure 2:
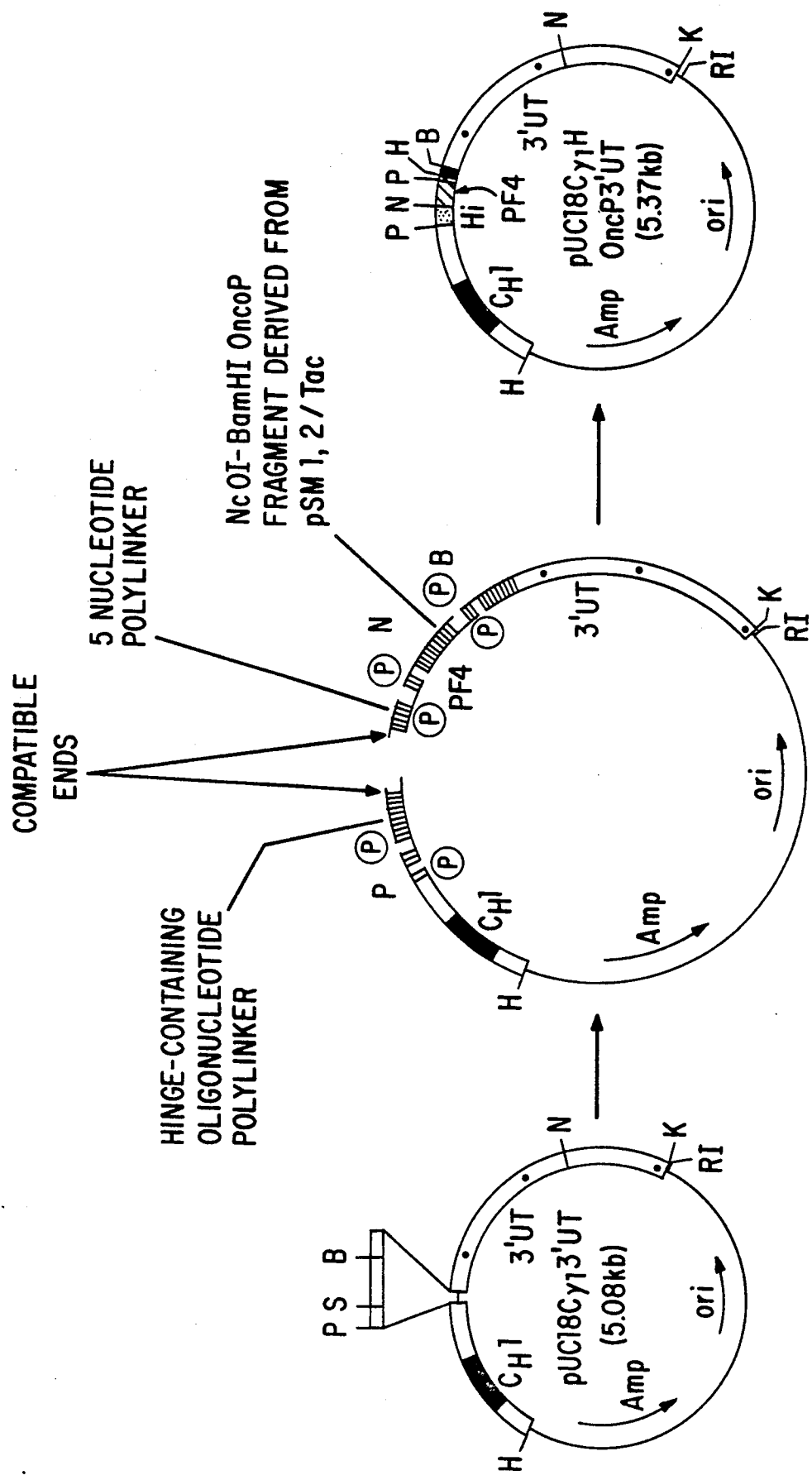

FIG. 2. Diagram of insertion of PF-4 cDNA into $CH_1$, Hinge-Bearing Vector.

Figure 3:
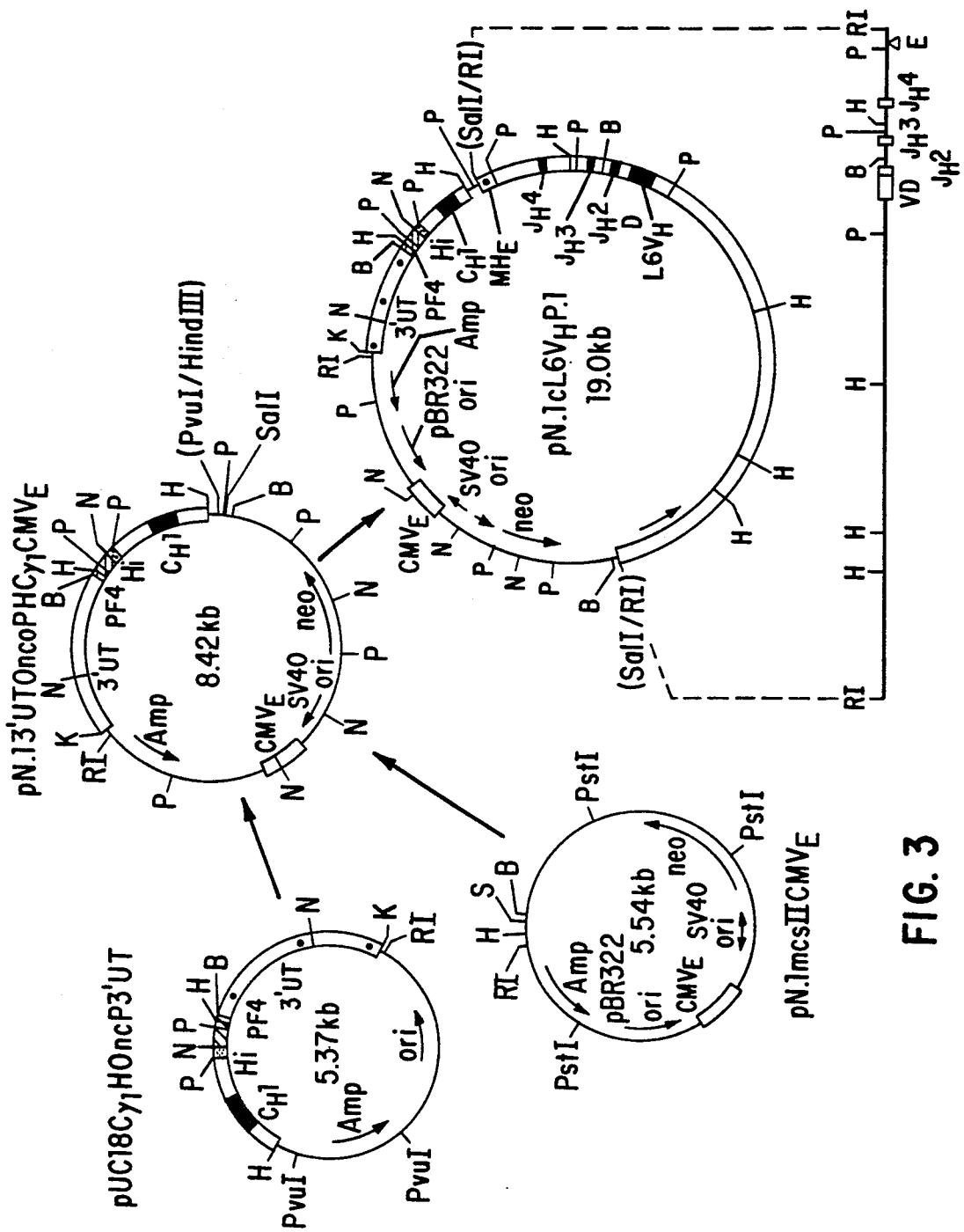

FIG. 3. Diagram of insertion of construct into a mammalian expression vector.

Figure 4:
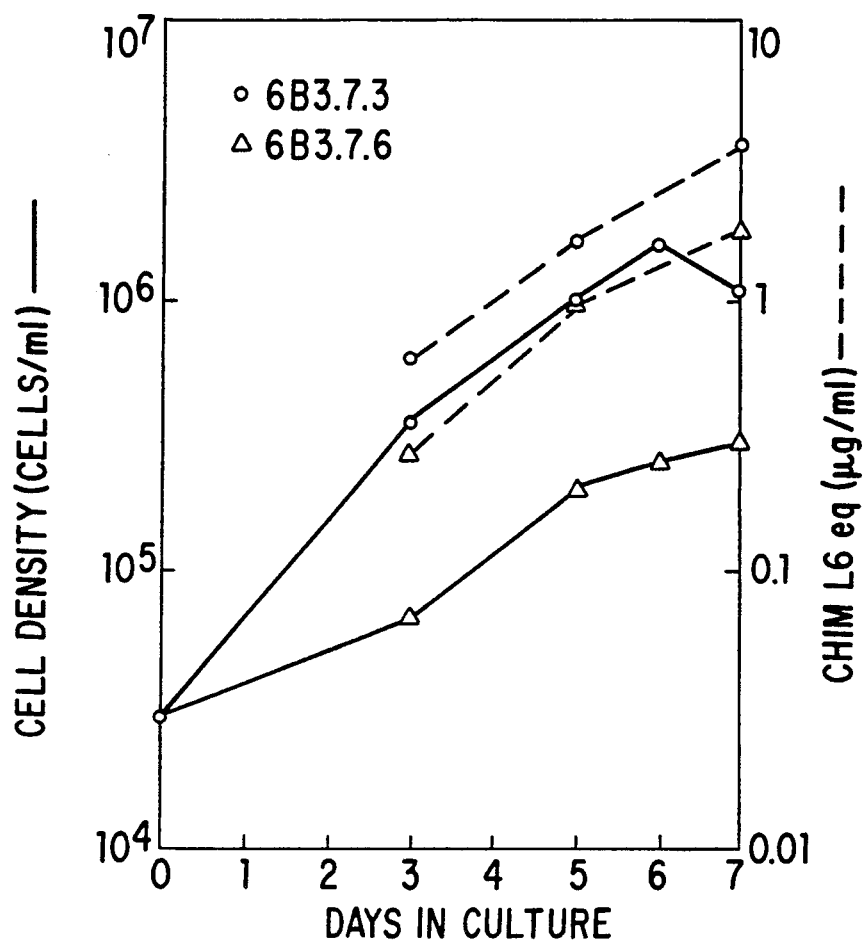

FIG. 4. Production of PF-4/L6 fusion protein by cell lines transfected with PF-4/L6 expression vector, as measured by reactivity with anti-L6 idiotype antibody.

Figure 5:
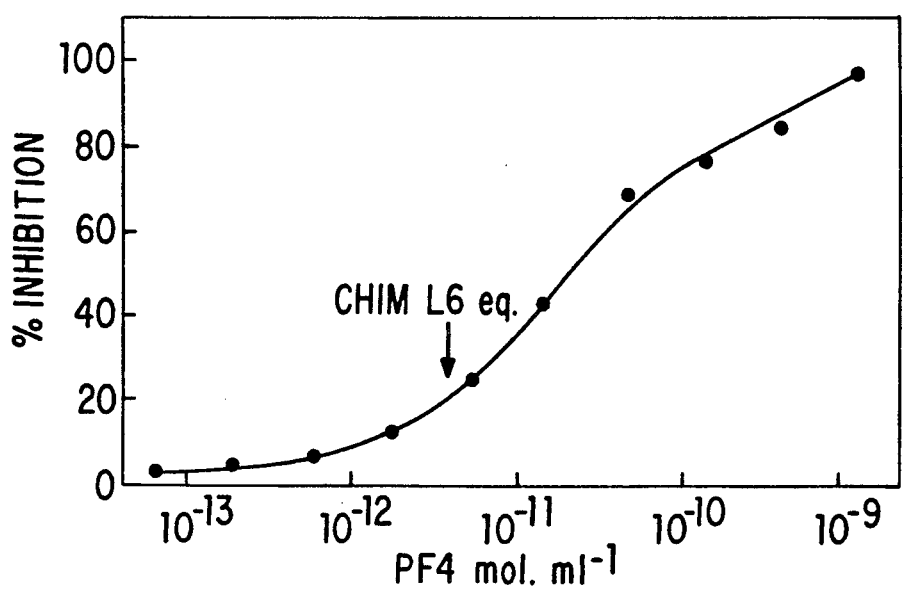

FIG. 5. Inhibition of binding of anti-PF-4 antibody to PF-4/L6 fusion protein by increasing concentrations of free PF-4.

Figure 6A:
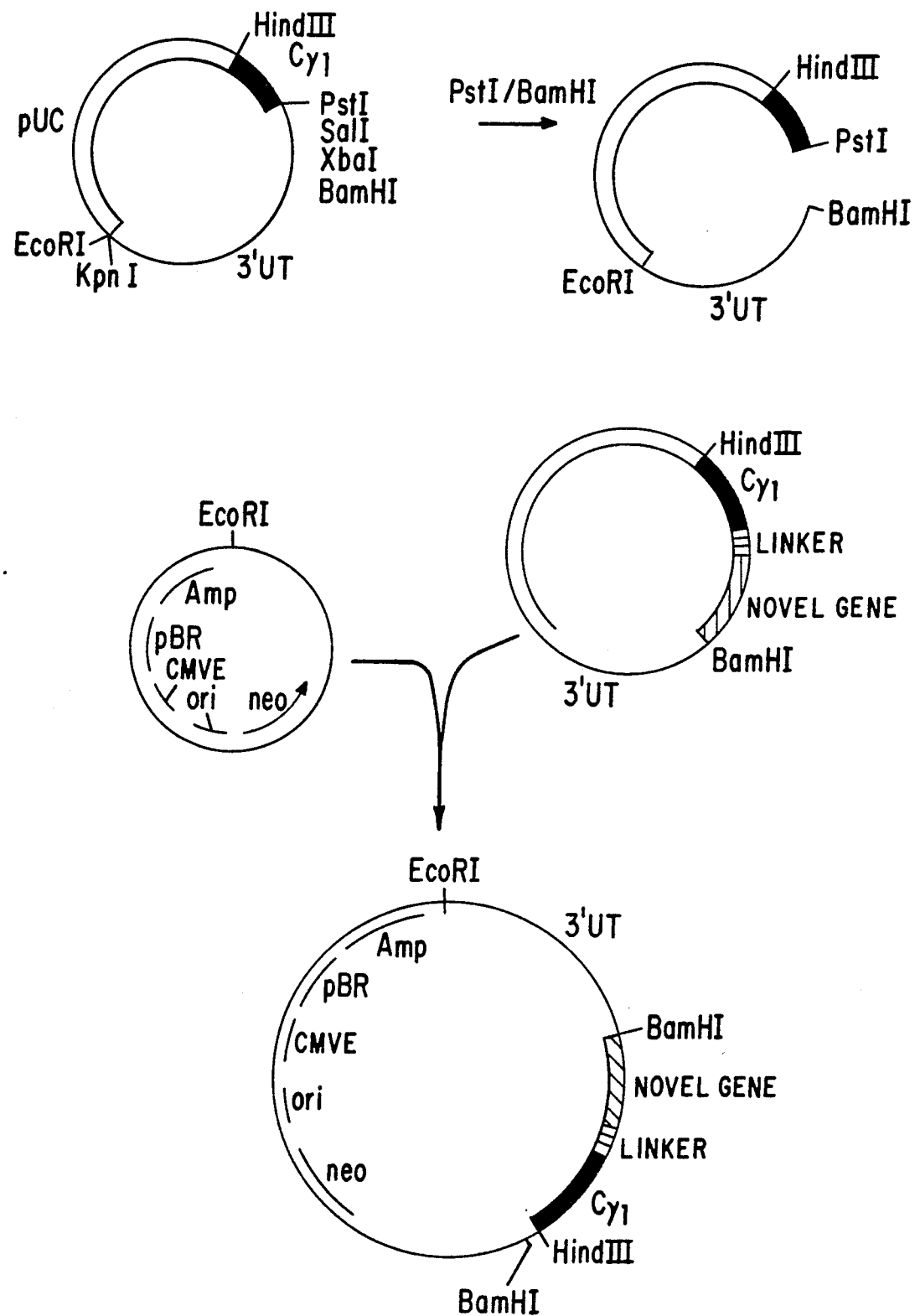
Figure 6B:
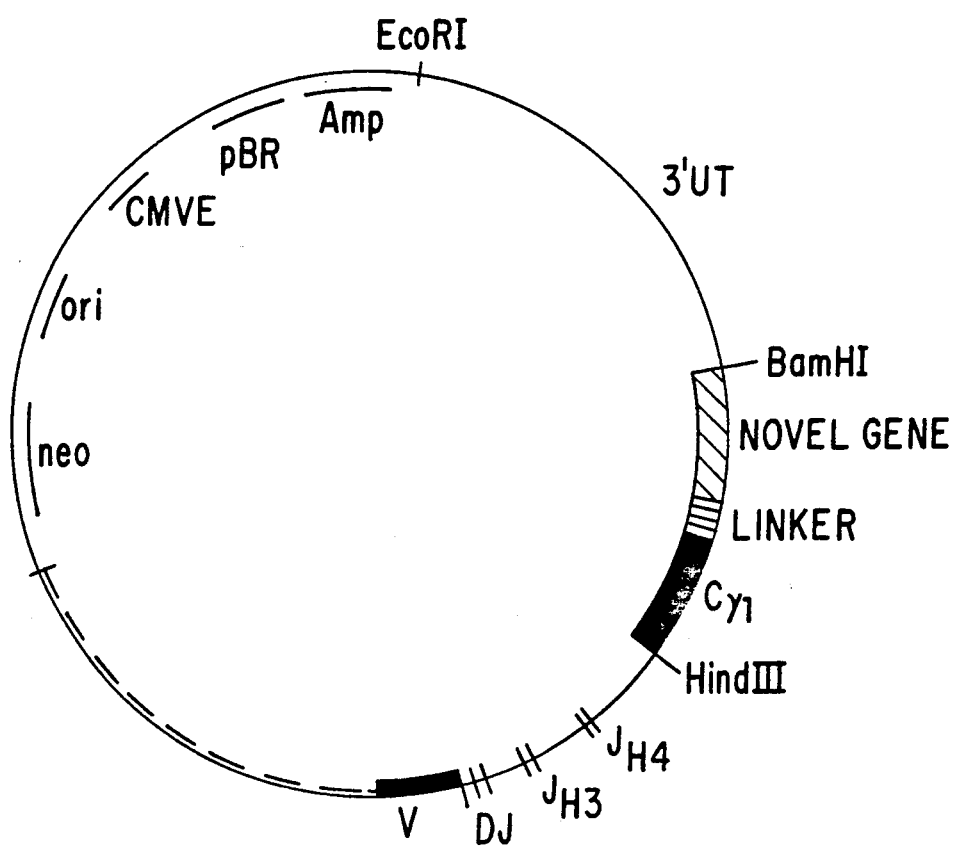

FIGS. 6A–6B. Diagram of strategy for the generation of IL-2/L6 fusion proteins. (a) insertion of IL-2 cDNA into pUC18 vector containing $C_{H1}$ and 3' untranslated regions (3'uT) from the mouse immunoglobulin gene locus with incorporation of hinge/linker sequences; (b) final expression vector comprising SV40$_{ori}$ promoter and the neo resistance gene.

FIG. 7. Exact hinge (a) and hinge-linker (b) sequences.

FIG. 8. Procedure of producing IL-2 cDNA for cloning.

FIG. 9. Coding portion of IL-2 amplified in polymerase chain reaction.

Figure 10:
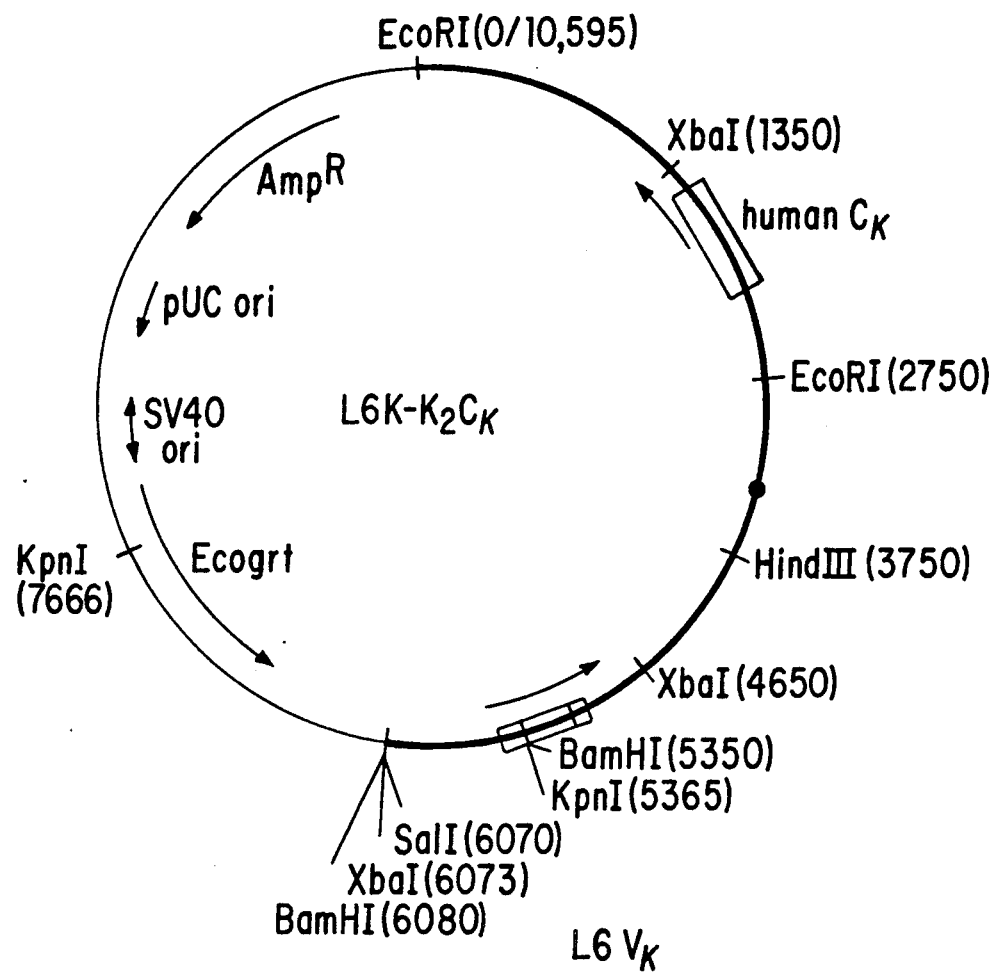

FIG. 10. Chimeric light chain vector cotransfected with pIL-2/L6.

5. DETAILED DESCRIPTION OF THE INVENTION

The present invention relates to a system for the generation of therapeutic antibody fusion proteins. In particular, the present invention relates to therapeutic antibody fusion proteins as well as the recombinant DNA molecules utilized in their production. For purposes of clarity of disclosure, and not by way of limitation, the detailed description of the invention will be divided into the following subsections:

(i) construction of recombinant genes encoding antibody fusion proteins;
(ii) expression of antibody fusion proteins; and
(iii) utility of the invention.

5.1. CONSTRUCTION OF RECOMBINANT GENES ENCODING ANTIBODY FUSION PROTEINS

The antibody-based fusion proteins of the invention comprise (i) a portion of an immunoglobulin molecule capable of directing the fusion protein to an intended cell or tissue and (ii) a biologically active protein or peptide. The recombinant genes encoding the antibody fusion proteins of the invention may be constructed using any technique known in the art of molecular biology, including but not limited to the following.

The targeting portion of the molecule may comprise all or part of an immunoglobulin variable region which may, in turn, be comprised of regions encoded by a V gene and/or D gene and/or J gene. In preferred embodiments of the invention, the antibody fusion proteins comprise a portion corresponding to the hinge region of an immunoglobulin molecule, or a functional equivalent thereof which would provide flexibility between the globular domains of the antibody-based fusion protein. A functional hinge may be important in retaining targeting ability. Variable regions of antibody, particularly monoclonal antibody, that recognize tumor-specific antigens, viral-specific antigens, bacterial antigens, parasite antigens, or antigens expressed on a particular population of cells (such as lymphocytes) may be used in fusion proteins of the invention.

Ligands which may be incorporated into the antibody-based fusion proteins of the invention include but are not limited to lymphokines and cellular factors which interact with specific cellular receptor. Lymphokines of the invention include but are not limited to interleukin-1 (Henderson and Pettipher, 1988, Biochem. Pharmacol. 37:4717); interleukin-2 (Weil-Hillman et al., 1988, J. Biol. Response Mod. 7:424); interleukin-6 (Van Damme et al., 1987, J. Exp. Med. 165:914-919); interferon α (Pitha et al., 19898, J. Immunol. 141:3611); and interferon γ (Blanchard and Djeu, 1988, J. Immunol. 141:4067).

Cellular factors which may be incorporated into the antibody-based fusion proteins of the invention include but are not limited to platelet factor 4 (Devel et al., 1981, Proc. Natl. Acad. Sci. U.S.A. 78:4584–4587); tumor necrosis factor α (Plate et al, 1988, Ann. N.Y. Acad. Sci. 532:149); epidermal growth factor (Carpenter and Cohen, A. Rev. Biochem. 48:193-216); fibroblast growth factor (Folkman and Klagsburn, 1987, Science 235:442–447); insulin-like growth factor-1 (Blundell and Humbel, 1980, Nature 287:781-787); insulin-like growth factor-2 (Blundell and Humbel, supra); platelet-derived growth factor (Ross et al., 1986, Cell 46:155-169); transforming growth factor α (Derynck, 1988 Cell 54:593-595); transforming growth factor β (Cheifetz et al., 1987, Cell 48:409–416); interferon β and nerve growth factor (Thoenen et al., 1982, in "Repair and Regeneration of the Nervous System", J. G. Nicholls, ed., Springer-Verlag, N.Y., pp. 173-185).

Recombinant nucleic acid molecules which encode the immunoglobulin, lymphokine or growth factor may be obtained by any method known in the art (Maniatis et al., 1982, Molecular Cloning; A Laboratory Manual, Cold Spring Harbor Laboratory, Cold Spring Harbor, N.Y.) or obtained from publicly available clones. For example, nucleic acid encoding a lymphokine or factor may be obtained as follows. A population of cells known to actively express the factor may be obtained, and total cellular RNA may be harvested therefrom. Amino acid sequence of the factor may be used to deduce the sequence of a portion of the factor's nucleic acid so as to design appropriate oligonucleotide primers, or, alternatively, the oligonucleotide primers may be obtained from a known nucleic acid sequence which encodes the factor. The oligonucleotide fragment may then be used in conjunction with reverse transcriptase to produce cDNA corresponding to factor-encoding nucleotide sequence (Okayama et al., 1987, Methods Enzymol. 154:3-29). The cDNA can then be cloned, and/or portions of the factor coding region may then be amplified from this cDNA using polymerase chain reaction and appropriate primer sequences, (Saiki et al., 1988, Science 239:487–491).

In particular embodiments of the invention, a recombinant vector system may be created to accommodate sequences encoding the ligand in the correct reading frame with a natural or synthetic hinge region. For example, and not by way of limitation, the hinge region of the human IgG$_1$ constant region may be used; in a specific embodiment of the invention, the constant region exon encoding the $C_{H1}$ domain of human IgG$_1$ may be cloned as a HindIII-PstI fragment into the vector pUC18 to which may be joined, using standard restriction enzyme techniques, a modified version of the human hinge region sequences of human IgG$_1$. In the modified version of the human hinge region, the two cysteine residues that normally mediate interchain disulfide linkage may be replaced by codons specifying proline and serine so as to permit greater flexibility in the fused molecule; in this specific embodiment the sequence of the hinge region may be EPKSCDKTHTPPPSPGRVVGGRA.

Additionally, it may be desirable to include, as part of the recombinant vector system, nucleic acids corresponding to the 3' flanking region of an immunoglobulin gene including RNA cleavage/polyadenylation sites and downstream sequences; according to a specific embodiment of the invention, this nucleotide sequence provides the mRNA with the 3' untranslated region of the secretory form of the murine Cμ gene. Furthermore, it may be desirable to engineer a signal sequence upstream of the antibody fusion protein-encoding sequences to facilitate the secretion of the fused molecule from a cell transformed with the recombinant vector.

Nucleic acid sequences encoding the various components of the antibody-based fusion proteins of the invention may be joined together using any techniques known in the art, including restriction enzyme methodologies and the use of synthetic linker sequences.

To provide for adequate transcription of the recombinant constructs of the invention, a suitable promoter/enhancer sequence may preferably be incorporated into the recombinant vector. Promoters which may be used to control the expression of the antibody-based fusion protein include, but are not limited to, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:144-1445), the regulatory sequences of the metallothionine gene (Brinster et al., 1982, Nature 296:39-42); prokaryotic expression systems such as the LAC, or β-lactamase promoter (Villa-Kamaroff, et al., 1978, Proc. Natl. Acad. Sci. U.S.A. 75:3727-3731), or the tac λ phage promoter (DeBoer, et al., 1983, Proc. Natl. Acad. Sci. U.S.A. 80:21-25), see also "Useful proteins from recombinant bacteria" in Scientific American, 1980, 242:74-94; plant expression vectors comprising the nopaline synthetase promoter region (Herrera-Estrella et al., Nature 303:209-213) or the cauliflower mosaic virus 35S RNA promoter (Gardner, et al., 1981, Nucl. Acids Res. 9:2871), and the promoter for the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phophatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene enhancers or promoters which are active in pancreatic beta cells (Hanahan, 1985, Nature 315:115-122), immunoglobulin gene enhancers or promoters which are active in lymphoid cells (Groschedl et al., 1984, Cell 38:647-658; Adames et al., 1985, Nature 318:533-538; Alexander et al., 1987, Mol. Cell. Biol. 7:1436-1444), the cytomegalovirus early promoter and enhancer regions (Boshart et al., 1985, Cell 41:521-530), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58); alpha 1-antitrypsin gene control region which is active in the liver (Kelsey et al, 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

Successful incorporation of antibody-based fusion gene constructs may be identified by three general approaches: (a) DNA-DNA hybridization, (b) presence or absence of "marker" gene functions, and (c) expression of inserted sequences. In the first approach, the presence of a foreign gene inserted in an expression vector can be detected by DNA-DNA hybridization using probes comprising sequences that are homologous to the inserted antibody fusion protein gene. In the second approach, the recombinant vector/host system can be identified and selected based upon the presence or absence of certain "marker" gene functions (e.g., thymidine kinase activity, resistance to antibiotics such as G418, transformation phenotype, occlusion body formation in baculovirus, etc.) caused by the insertion of foreign genes in the vector. For example, if the antibody fusion gene is inserted so as to interrupt the marker gene sequence of the vector, recombinants containing the antibody fusion gene insert can be identified by the absence of the marker gene function. In the third approach, recombinant expression vectors can be identified by assaying the foreign gene product expressed by the recombinant. Such assays can be based, for example, on the physical or functional properties of the antibody fusion gene product in bioassay systems as described infra.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus, adenovirus or retroviral based vectors; insect viruses such as baculovirus; yeast vectors; bacteriophage vectors (e.g., lambda), and plasmid and cosmid DNA vectors, to name but a few.

In a preferred embodiment of the invention, the promoter/enhancer and 3' regulatory sequences may all be derived from immunoglobulin genes.

5.2. EXPRESSION OF ANTIBODY FUSION PROTEINS

The recombinant constructs of the invention may be introduced into host cells which are capable of expressing the antibody-based fusion protein using any method known in the art, including transformation (for example, using DEAE-dextran or calcium phosphate techniques), transfection, microinjection, infection, cell gun, and electroporation. Any host cell type may be utilized provided that the antibody-based fusion protein recombinant nucleic acid sequences would be adequately transcribed into mRNA in that cell type. In specific embodiments of the invention, mouse myeloma cell lines which do not produce immunoglobulin, such as Sp2/o or Ag8.653 may be used. In addition, the recombinant nucleic acid constructs of the invention may be used to create non-human transgenic animals capable of producing the antibody based fusion protein. In preferred embodiments of the invention, the host cell is a lymphoid cell. In specific embodiments of the invention, the host cell is a hybridoma derived heavy chain loss variant which expresses immunoglobulin light chains; in this embodiment, the parent hybridoma most preferably may be the source of the monoclonal antibody which comprises the immunoglobulin portions of the antibody-based fusion protein. Thus, for example, and not by way of limitation, the light-chain producing cell line derived from a hybridoma which produces monoclonal antibody "X" may be transfected with recombinant DNA encoding an antibody-based fusion protein which comprises a variable region of monoclonal antibody "X"; the antibody-based fusion protein may combine with endogenous light chain and thereby re-create the antigen binding site of monoclonal antibody "X".

Alternatively, recombinant nucleic acids encoding both antibody-based fusion protein and corresponding or compatible immunoglobulin light chain may be co-transfected into a cell line which is preferably of lymphoid origin. In yet a further embodiment of the invention, the antibody fusion protein encoding sequences may be introduced into the immunoglobulin locus of a lymphoid cell line by homologous recombination according to methods set forth in U.S. patent application Ser. No. 07/242,873, by Folger-Bruce and Fell, filed Sep. 14, 1988, which is incorporated by reference in its entirety herein.

Antibody-based fusion protein produced by the host cell may be collected using any technique known in the art, including, but not limited to, affinity chromatography using target antigen or antibody specific for any portion of the fusion protein including, for example, anti-idiotype antibody. The activity of the fused lymphokine or cellular factor may be confirmed using biological assays which detect or measure the activity of the lymphokine or cellular factor. For example, and not by way of limitation, if IL-2 is the lymphokine comprised by the antibody fusion protein, the presence of IL-2 activity may be confirmed in assays which detect T-cell proliferation. In a specific embodiment of the invention, the presence of PF4 activity is confirmed by observing that the antibody fusion protein binds to anti-PF4 antibody in a manner which is competitively inhibited by free, unconjugated PF4 protein.

The present invention provides for dimeric immunoglobulin molecules as well as monomeric or multimeric molecules comprising antibody based fusion proteins.

5.3. UTILITY OF THE INVENTION

The present invention provides for antibody based fusion proteins that may be used to deliver biologically active ligand molecules to specific target cells or tissues. In particular embodiments of the invention, the antibody fusion proteins comprise ligands which are lymphokines or other cellular factors.

In various embodiments of the invention, an antibody fusion protein may comprise variable region sequences which recognize a tumor specific antigen. According to a specific embodiment of the invention, the variable region sequences are derived from L6, a monoclonal antibody which reacts with an antigen present on human nonsmall cell lung carcinoma and a number of other carcinomas, including breast and colon carcinoma. If the antibody fusion molecule which recognizes a tumor specific antigen also comprises a lymphokine, it may be used to alter the immune response in the area of the tumor cells. For example, as shown in Example Section 7, infra, an antibody fusion protein comprising IL-2 and the L6 variable region retains IL-2 activity. The IL-2/L6 fusion protein may be used to target IL-2 to tumor cells; consequently, activated T-cells in the vicinity of the tumor will be induced to proliferate, thereby amplifying the anti-tumor immune response. It should be noted that current immunotherapy often involves systemic administration of lymphokines at a concentration that is intended to effectively boost anti-tumor activity but which necessarily affects lymphocytes and tissues throughout the body. In the case of IL-2, severe and potentially fatal clinical reactions may occur. The present invention offers the advantage of decreasing systemic exposure to lymphokine; antibody-mediated targeting allows for less total lymphokine to be administered and substantially decreases the exposure of non-tumor tissues to lymphokine, thereby minimizing toxic effects. In a further specific embodiment, a PF4/L6 antibody may be used to inhibit angiogenesis at a tumor site and thereby inhibit tumor growth.

In additional embodiments, the antibody fusion proteins of the invention may be directed toward antigens associated with infectious agents, including viral, bacterial, or parasitic antigens. In a specific embodiment, the antibody fusion protein may comprise a chemotactic factor which may be used to recruit polymorphonuclear leukocytes to sites of infection, including the walls of abscesses.

Alternatively, the antibody fusion proteins of the invention may be directed toward antigens present on a subpopulation of cells in the body. For example, antibody fusion proteins directed toward antigens on the surface of helper T-cells could be used to target ligands which augment helper cell activity in immune compromised patients or to target ligands that down regulate T-helper responses in cases of autoimmunity. Alternatively, antibody fusion proteins directed toward antigens on the surface of suppressor T-cells may be used to regulate activity. Subpopulations of cells could also be targeted based on receptor specificity (e.g. antigen for lymphocytes).

In additional embodiments of the invention, cellular factors that relate to wound healing may be incorporated into antibody fusion proteins. For example, fibroblast growth factor may be combined with an antibody which recognizes an antigen exposed by or applied to an area of cell injury.

The antibody fusion proteins may be administered to a patient in need of such treatment in any sterile pharmaceutical carrier which will maintain the solubility and activity of the protein. It may be desirable to administer antibody fusion proteins in conjunction with other treatment modalities, including antibodies and/or antibody fusion proteins comprising additional growth factors.

6. EXAMPLE: CONSTRUCTION AND EXPRESSION OF A PLATELET FACTOR 4/L6 ANTIBODY FUSION PROTEIN WITH PLATELET FACTOR 4 ACTIVITY

6.1. MATERIALS AND METHODS

6.1.1. CONSTRUCTION OF AN EXPRESSION CASSETTE FOR AN ANTIBODY-BASED FUSION PROTEIN

A recombinant vector system was created to accommodate sequences encoding novel protein structure in the correct reading frame with the hinge region of the human IgG$_1$ constant region. Initially, the constant region exon encoding the C$_{H1}$ domain of human IgG$_1$ was cloned as a HindIII/PstI fragment into the vector pUC18 (FIG. 1). Downstream of these sequences was cloned a 1.6 kb PstI/KpnI fragment containing a portion of the 3' flanking region of the murine C$\mu$ gene that includes the RNA cleavage/polyadenylation sites used in the expression of mRNA encoding the secretory form of IgM heavy chain. A portion of the vector polylinker was retained between the two fragments for subsequent additions.

A pair of oligonucleotides was generated that when annealed encode a modified version of the human hinge region sequences of human IgG$_1$. The two cysteines that normally mediate interchain disulfide linkage between heavy chains were replaced with codons specifying proline and serine, and several amino acids were added to the carboxy terminus such that the entire hinge region sequence is: EPKSCDKTHTPPPSPGRVVG-GRA. The annealed oligonucleotide pair has a PstI compatible overhang on the 5' end, includes the normal splice acceptor site for the hinge exon, and retains another suitable overhang for linkage with additional oligonucleotides at the 3' end. A second pair of oligonucleotides was designed to overlap with the first set and provide compatible ends for ligation with an NcoI overhang.

6.1.2. INSERTION OF PLATELET FACTOR 4 ENCODING SEQUENCES INTO ANTIBODY FUSION PROTEIN CASSETTE

The cDNA clone encoding human platelet factor 4 (PF$_4$) was linked as an NcoI/BamI fragment in frame with the hinge region by ligation into the PstI/BamI sites of the vector with the two pairs of oligonucleotides at the 5' end (FIG. 2). The fusion construct was then transferred to a vector that contains a dominant selectable marker (NEO) for expression in mammalian cells (FIG. 3), and then a gene segment encoding a heavy chain variable region of the desired specificity was inserted just upstream.

6.1.3. EXPRESSION OF PLATELET FACTOR 4/L6 FUSION PROTEIN

The construct was transfected into a murine myeloma cell line expressing the chimeric light chain and supernatants were screened for production of heavy/light assembled protein using anti-idiotypic antibodies specific for L6 V region determinants. Clones were established that tested positive for the presence of assembled heavy and light chain.

6.2. RESULTS AND DISCUSSION

The first example of an immunoglobulin fusion protein generated by this design incorporated the sequence of human platelet factor 4 downstream as part of the L6 chimeric heavy chain. Platelet factor 4 has been reported to have several biological activities of interest including heparin binding, antagonism of angiogenesis, inhibition of suppressor T lymphocyte development, chemotaxis for inflammatory cells, etc.

The growth and production characteristics (as determined by the Id/Id assay) for two clones are shown in FIG. 4. As can be seen by comparison with purified chimeric L6 as a standard, substantial amounts of Id bearing protein is produced, although it should be emphasized that chimeric L6 is a bivalent molecule that probably reacts somewhat differently than a chimeric F(ab) in this assay.

Culture supernatants from a clonal cell line were used to establish the PF4 nature of the heavy chain fusion protein. ELISA plates were coated with goat antisera specific for human platelet factor 4 (a kind gift from Dr. Karen Kaplan, Columbia University). Supernatant from the producing clone was then added jointly in the presence of various concentrations of purified PF4 protein (Sigma), or media only. The plate was subsequently developed with the biotinylated 13B anti-idiotype which recognizes an L6 combinatorial determinant, and avidin-HRP (TAGO). FIG. 5 shows a plot of the percent inhibition of the detectable signal with increasing amounts of the PF4 protein. No inhibition was observed by coincubation with chimeric L6 protein.

Since PF4 is normally capable of binding to heparin, that biological activity was characterized for the assembled fusion protein. Culture supernatant or media spiked with chimeric L6 protein was adsorbed on heparinsepharose. The amount of assembled protein was measured by an anti-Id assay requiring the presence of both light chain and combinatorial determinants (15B capture and 14B biotinylated to detect). The concentration before and after incubation with heparin-sepharose is shown in Table 1,

TABLE 1

| Adsorption of L6PF$_4$ and ChimFab to Heparin-Sepharose | | | |
|---|---|---|---|
| | Conc (ng/ml)[1] | | Heparin bound |
| Sup | Before ads | After ads | (%) |
| 6B3.7subc16 | 137 | <5 | <96 |
| ChimFab | 64 | 64 | 0 |

[1]Expressed in ChimL6 eq. (15B - 14 Bbio Elisa)

demonstrating that greater than 95% of the assembled Ig fusion protein is removable by heparin, a property not associated with the chimeric L6 molecule. The L6/PF4 fusion protein was also shown to bind to human tumor cells by FACS analysis using antisera specific for human Fab or human PF4.

These studies demonstrate that the basic design described here is useful for generating heavy chain fusion proteins that maintain dual characteristics and can be expressed at reasonable levels.

7. EXAMPLE: CONSTRUCTION AND EXPRESSION OF AN INTERLEUKIN-2/L6 ANTIBODY FUSION PROTEIN HAVING INTERLEUKIN-2 ACTIVITY

7.1. MATERIALS AND METHODS

7.1.1. CONSTRUCTION OF AN EXPRESSION VECTOR FOR THE IL-2 ANTIBODY FUSION PROTEIN

A slightly different strategy was employed for the generation of L6/IL2 fusion protein, shown in FIG. 6. These constructs began with the same pUC18C gammal 3'UT shown in FIG. 2. This vector was opened with PstI and BamHI to receive three DNA fragments. The first fragment was a pair of oligonucleotides encoding a modified version of the human hinge region in which the cysteines that normally mediate intermolecular linkage to another heavy chain have been replaced with codons specifying proline and serine (shown as hinge in FIG. 7). The second section was formed by another pair of oligonucleotides (IL2 hinge gene linker sequence in FIG. 7) that has a 5' compatible overhang with that of the hinge pair, and a 3' overhang compatible with that of NcoI. This restriction site encompasses a codon specifying methionine and had been used for cloning the PF4 gene into bacterial expression vectors. The third component was the segment encoding the desired effector function (novel gene in FIG. 6) with an NcoI overhang at the 5' end and a BamHI overhang at the 3' end to complete ligation into the vector.

A separate construct was created by using oligonucleotides that encode each of the three cysteines normally present in the human IgG$_1$ hinge region, but with a stop codon immediately following the hinge sequence (FIG. 7 (Fab')$_2$)

Each assembled sequence was then transferred as a HindIII/Eco RI fragment to a vector containing a dominantly selectable gene (NEO) for transfection into eukaryotic cells. Subsequent to this step, either the cloned fragment encoding the L6 heavy chain variable region, or the 2.3 kb HindIII fragment used for direct gene targeting to the IgH locus, was cloned just upstream.

In the case of IL2, the coding region was generated using the polymerase chain reaction (PCR). The overall procedure is outlined in FIG. 8. Peripheral blood cells from normal human donors were stimulated for 6 hours with anti-CD3 and anti-CD28 to elicit the production of IL2 RNA by the T cells within the population. Total cellular RNA was then extracted from these cells and a single strand cDNA copy of the IL2 message was generated using primer IL2-3' as shown in FIG. 8. The portion of the IL2 coding region specified in FIG. 9 was amplified from this cDNA by the polymerase chain reaction using the primers IL2-5' and IL2-3' (FIG. 8). The 3' portion of each primer is perfectly homologous to the IL2 sequence, whereas the 5' region of each primer is mismatched to include an NcoI site at the 5' end and a BamHI site at the 3' end of the final product. This PCR product was cloned as a blunt fragment into the SmaI site of pUC19 for sequencing. Once the IL2 sequence was confirmed the coding region was transferred as an NcoI/BamHI fragment to the pUC18-Cgamma 13' UT plasmid as described above.

7.2. RESULTS AND DISCUSSION

7.2.1. EXPRESSION OF IL-2/L6 ANTIBODY FUSION PROTEIN

The L6/IL2 heavy chain fusion vector was cotransfected along with the chimeric light chain vector shown in FIG. 10 into either the Ag8.653 or Sp2/0 non-Ig producing murine plasmacytoma cell line. Selection was performed using G418 and resistant cell populations were tested for production of both heavy and light chain using a pair of anti-idiotypes, one specific for the L6 light chain variable region and the other specific for the heavy chain variable region of L6. A single clone from the Ag8 transfection (10$^3$A4) was chosen for further study.

7.2.2. ASSAYS FOR BIFUNCTIONAL ACTIVITY OF THE FUSION PROTEIN

Culture supernatant from this cell line was used to demonstrate the dual functionality of the fusion protein in the following way. The human tumor cells ($1 \times 10^4$) that bear the L6 antigen were irradiated and incubated with either media, 20 $\mu$/ml of chimeric L6, 10$^3$A4 supernatant, supernatant plus 20 $\mu$/ml of murine L6 antibody, or supernatant plus 20 $\mu$/ml of L6 anti-idiotype 14B. The cells were incubated for 30 minutes on ice, washed, and then mixed with $2 \times 10^4$ CTLL-2 cells which proliferate in response to IL2. The proliferation was measured as a function of $^3$H-thymidine incorporation and the results were as follows:

TABLE I

| 3347s w/ | CPM | % INHIB |
|---|---|---|
| Media | 8950 | |
| cL6 | 12151 | |
| 10$^3$A4 Sup | 78731 | |
| Sup + L6 | 11238 | 97 |
| Sup + anti-id | 13690 | 93 |

8. DEPOSIT OF MICROORGANISMS

The following microorganisms have been deposited with the Agricultural Research Culture Collection. Northern Regional Research Center (NRRL) 1815 No. University Street, Peoria, Ill., 60604 and have been assigned the following accession numbers:

| microorganism | plasmid | Accession No. |
|---|---|---|
| DH5α | pPF-4/L6 | B-18595 |
| DH5α | pIL-2/L6 | B-18589 |

The cell line, designated L6, which produces the L6 monoclonal antibody was deposited with the American Type Culture Collection (ATCC), 12301 Parklawn Drive, Rockville, Md., 20852 on Dec. 6, 1984 and received accession number HB 8677.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Various publications are cited herein, the disclosures of which are incorporated by references in their entireties.

What is claimed is:

1. An antibody-based fusion protein wherein a portion of an immunoglobulin molecule comprising a variable region capable of binding to a tumor-associated antigen is joined via peptide linkage to an Il-2 molecule capable of promoting lymphocyte proliferation.

2. The fusion protein of claim 1 wherein the variable region is derived from monoclonal antibody L6 produced by hybridoma ATCC HB 8677.

3. A fusion protein produced by the cell line DH5α carrying plasmid pIL-2/L6 as deposited with the NRRL under Accession No. B-18589.

* * * * *